US009480633B2

(12) United States Patent
Paulsen et al.

(10) Patent No.: US 9,480,633 B2
(45) Date of Patent: Nov. 1, 2016

(54) TEMPERATURE MANAGEMENT COMPOSITION

(75) Inventors: Jeremy D. Paulsen, Neenah, WI (US); Scott W. Wenzel, Neenah, WI (US); Rafael Ignacio Giganti, Buenos Aires (AR); Corey T. Cunningham, Larsen, WI (US); Jeffery R. Seidling, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 173 days.

(21) Appl. No.: 13/096,677

(22) Filed: Apr. 28, 2011

(65) Prior Publication Data

US 2012/0276033 A1 Nov. 1, 2012

(51) Int. Cl.
| | | |
|---|---|---|
| *A61K 8/34* | (2006.01) | |
| *A61Q 15/00* | (2006.01) | |
| *A61K 8/37* | (2006.01) | |
| *A61K 8/42* | (2006.01) | |
| *A61K 8/49* | (2006.01) | |
| *A61K 8/97* | (2006.01) | |

(52) U.S. Cl.
CPC .............. *A61K 8/34* (2013.01); *A61K 8/345* (2013.01); *A61K 8/37* (2013.01); *A61K 8/42* (2013.01); *A61K 8/4926* (2013.01); *A61K 8/97* (2013.01); *A61Q 15/00* (2013.01); *A61K 2800/244* (2013.01)

(58) Field of Classification Search
CPC ... A61K 8/34; A61K 2800/244; A61Q 15/00
USPC ........................................................ 424/401
See application file for complete search history.

(56) References Cited

U.S. PATENT DOCUMENTS

| | | | |
|---|---|---|---|
| 3,555,145 A * | 1/1971 | Wetzel ................ | A61K 8/19 424/47 |
| 4,264,586 A | 4/1981 | Callingham et al. | |
| 5,348,735 A * | 9/1994 | Harris et al. ................. | 424/65 |
| 6,277,385 B1 | 8/2001 | Luke | |
| 2002/0106340 A1 | 8/2002 | Guskey | |
| 2003/0198680 A1 | 10/2003 | Shefer et al. | |
| 2004/0082654 A1 | 4/2004 | Pesce et al. | |
| 2005/0053632 A1 | 3/2005 | Schafer et al. | |
| 2005/0265930 A1 | 12/2005 | Erman et al. | |
| 2006/0067961 A1 | 3/2006 | Krzysik et al. | |
| 2008/0085247 A1 | 4/2008 | Langner et al. | |
| 2008/0124282 A1 | 5/2008 | Emmerling et al. | |
| 2008/0188560 A1 | 8/2008 | Mohammadi et al. | |
| 2008/0267889 A1 | 10/2008 | Cernasov et al. | |
| 2009/0092688 A1 | 4/2009 | Williams et al. | |
| 2009/0110656 A1 | 4/2009 | Lemke et al. | |
| 2009/0220444 A1 * | 9/2009 | Teckenbrock et al. ........ | 424/66 |
| 2010/0292294 A1 | 11/2010 | Watson et al. | |

FOREIGN PATENT DOCUMENTS

| | | |
|---|---|---|
| EP | 0 673 403 B1 | 7/1997 |
| GB | 1 300 399 A | 12/1972 |
| JP | 05-271100 A | 10/1993 |
| WO | WO 96/18378 A2 | 6/1996 |
| WO | WO 98/56340 A1 | 12/1998 |
| WO | WO 00/45815 A1 | 8/2000 |
| WO | WO 2009/049190 A1 | 4/2009 |
| WO | WO 2009/087242 A2 | 7/2009 |
| WO | WO 2009/140783 A1 | 11/2009 |

* cited by examiner

*Primary Examiner* — Michael B Pallay
(74) *Attorney, Agent, or Firm* — Kimberly-Clark Worldwide, Inc.

(57) ABSTRACT

The present invention relates to a single phase temperature management composition. The composition includes from 0.01% to 10% by weight of a neurosensory agent and from 0.01% to 30% by weight of an antiperspirant component. The composition also includes a polar carrier where the polar carrier includes water and monohydric alcohol. The ratio of water to monohydric alcohol ranges from 0.0625:1 to 1.5:1. The compositions of the invention have a viscosity at room temperature of less than 2500 centipoise.

10 Claims, 1 Drawing Sheet

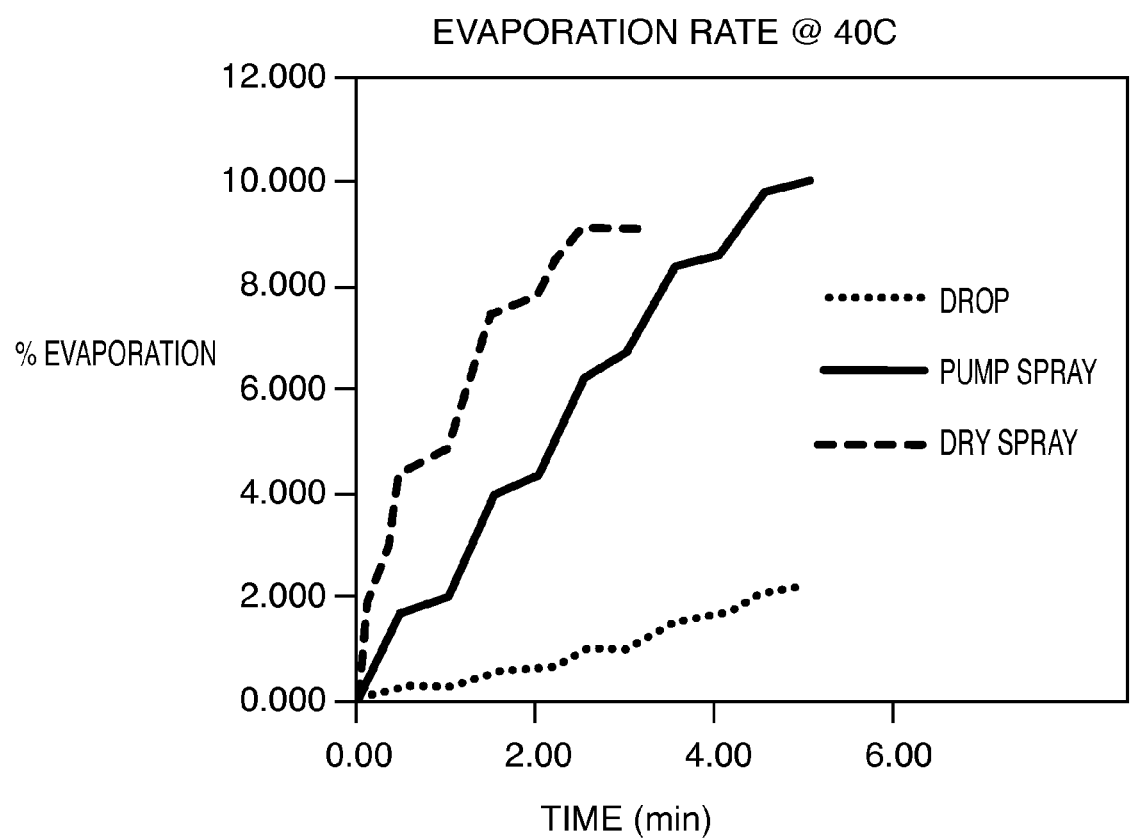

US 9,480,633 B2

TEMPERATURE MANAGEMENT COMPOSITION

FIELD OF THE INVENTION

The present invention relates to compositions that alleviate discomfort experienced by women during a hot flash. The compositions of the invention are single phase and do not need to be dispensed using aerosol packaging. The compositions include a neurosensory agent, an antiperspirant component and a polar carrier. The polar carrier includes water and one or more monohydric alcohols. The compositions have a ratio of water to monohydric alcohol of from 0.0625:1 to 1.5:1. The compositions of the invention alleviate discomfort experienced during a hot flash, especially the feeling of intense heat, by providing a cool sensation and an antiperspirant effect in the form of a temperature management spray.

BACKGROUND OF THE INVENTION

Many physiological changes are experienced as women go through menopause. It is believed that a significant majority, perhaps as high as 80 percent, of women experience the discomfort of the "hot flash/flush" associated with menopause. A hot flash is believed to be the result of the hormonal changes, particularly the decline in estrogen levels that occurs during menopause. Although some sources differentiate between a "hot flash" and "hot flush," both conditions will be referred to herein collectively as "hot flash" or "hot flashes." A hot flash is marked by an increase in body temperature accompanied by an intense feeling of unbearable heat, particularly internally radiating body heat. A hot flash may also be accompanied by an increase in heart rate, dizziness, anxiety, faintness, a sense of unease, tingling sensations, pressure in the head, nausea, perspiration, and feelings of breathlessness. The feeling of heat is often concentrated in the area of the face and neck, and sometimes spreads to the area of the upper chest. Although a hot flash may last for as short as a minute, a hot flash usually lasts as long as two to three minutes, and may last as long as an hour. Regardless of the duration of the hot flash, the discomfort due to the intense feeling of heat is extremely uncomfortable and disconcerting to a woman experiencing the hot flash.

When a woman experiences a hot flash, the first detectable change is an increase in finger blood flow with a concomitant enhancement of skin conductance, as well as a change in temperature of the skin of the face and neck. The increase in skin conductance is followed rapidly by a sharp rise (1-7° C.) in finger temperature. The degree to which finger temperature rises during a hot flash is inversely proportional to the base-line finger temperature before the flash. Thus, a 0.50° C. increase in finger temperature in a woman with a base-line finger temperature of 35° C. may be as good a measure of the occurrence of a hot flash as a 5° C. increase in finger temperature in a woman with base-line finger temperature of 29° C., because of the non-linear relationship between skin temperature and blood flow. As vasodilation and sweating ensue, internal body temperature drops. The magnitude of decrease in core temperature ranges from 0.10° C. to 0.90° C. The onset of sweating is rapid and is particularly profuse in the face and scalp. It may occur in five minute bursts accompanying short, discrete hot flashes, or continue in waves for more than thirty minutes during prolonged hot flashes. A hot flash is the inverse of a fever. In mammals, the control of body temperature resembles a negative feedback system in which a set point temperature serves as reference for the thermoregulatory mechanism. A fever can be understood as the upward adjustment of this temperature set point. In a febrile episode, the set point is first elevated, initiating vasoconstriction, shivering and behavioral modifications, such as the addition of blankets. This results in an elevation of body temperature to a level that is maintained for a period of time. A hot flash, on the other hand, is a transient downward adjustment of the set point, which results in the sensation of heat. At the end of a hot flash, the set point returns to normal. The trigger for a change in set point may be a series of nerve impulses. A fever, even with a rapid onset, may last for hours, days or even weeks. In contrast, the duration of a hot flash is in the order of minutes.

A number of products, systems and methods are known for eliminating hot flashes and/or for alleviating the effects of hot flashes. Some of the known approaches involve application of a composition to the skin. Often, the compositions include ingredients that are not miscible with each other and, therefore, the compositions are multi-phase. With more than one phase, there is always the possibility of destabilization and separation. Additionally, the known compositions are often delivered via a pressurized (i.e. aerosol) dispensing container. Aerosol packaging may have one or more disadvantages including higher cost, environmental concerns and inhalation concerns. Further, because of the mode of dispensing, there may be limitations on the ingredients that can be dispensed from aerosol packaging. In providing a product to alleviate the symptoms of hot flashes, the vehicle by which the product is delivered to the user should be harmonious with the initial signs and spread of hot flash symptoms. Hot flashes are most commonly associated with the discomforting symptom of an intense feeling of heat that begins in the face, neck, or chest regions and then radiates to other parts of the body. However, prior to the intense feeling of heat, many women experience a premonition of an impending hot flash that is accompanied by symptoms, such as a feeling of unease or anxiety, a feeling of pressure in the head, or tingling sensations. During this time, there is a concurrent increase in heart rate, digital blood flow, and vasodilation of blood vessels of the skin. At this point, women will experience an intense feeling of heat which may further be accompanied by feelings of dizziness, nausea and breathlessness. For most women who experience hot flashes, these foregoing symptoms are very unpleasant. Indeed, for some women the extent of these symptoms experienced during a hot flash can be downright unbearable. In order to respond to and alleviate the discomfort associated with the initial symptom of the intense feeling of heat that begins in the face, neck and/or chest, it would be desirable to provide a composition that lends itself to convenient topical application to the skin of these body areas.

Known compositions that are formulated to alleviate the discomfort associated with hot flashes often include volatiles like ethanol to provide immediate cooling, but the relief provided by such compositions dissipates quickly. The period of relief may be extended by also including a neurosensory agent, such as menthol. However, the scent associated with the neurosensory agent may not be pleasant and a neurosensory agent such as menthol may begin to irritate the skin of the user if used for a prolonged period. Another approach taken in known compositions is to use a phase change material to provide a cooling effect, but as with volatiles, the soothing effect may not last very long. Further, these traditional "cooling agents" do not address the sweating that occurs with hot flashes. In order to address the sweating, an antiperspirant salt may be added to the composition. However, the antiperspirant salts are generally used at a relatively high level to stop the sweating which may cause skin irritation—particularly when the composition is being applied over a larger skin surface area.

While compositions for alleviating the symptoms of hot flashes are known, there remains a need in the art for a temperature management composition that provides a cooling effect and prevents sweating for a period of greater than one minute. Additionally, there remains a need for a temperature management composition that is single phase and does not need to be applied using aerosol packaging. Further, there remains a need for a temperature management composition that is not irritating to the skin with regular use and that can be used on a relatively large area of the skin surface of the user.

SUMMARY OF THE INVENTION

The present invention relates to a single phase temperature management composition. The composition includes from 0.01% to 10% by weight of a neurosensory agent and from 0.01% to 30% by weight of an antiperspirant component. The composition also includes a polar carrier including water and a monohydric alcohol. The ratio of water to monohydric alcohol is from 0.0625:1 to 1.5:1. The ratio represents the weight percent of water to the weight percent of monohydric alcohol. The composition has a viscosity of less than 2500 centipoise at room temperature. The temperature management compositions of the invention are intended for alleviating the symptoms associated with menopause, including night sweats associated with "hot flashes". The compositions are easily applied to the user's skin at room temperature and the compositions do not require a propellant for application. The compositions may be provided to the end user using aerosol packaging; in this case, the additional components needed to provide the propellant effect should be compatible with the claimed components of the temperature management composition. Further, the compositions of the invention are a single phase, aqueous system. Suitable monohydric alcohols for use in the compositions of the invention include ethanol, propanol and butanol—both the straight chain and branched forms of these alcohols. The neurosensory agent and the monohydric alcohol of the polar carrier provide a cooling sensation to the user's skin and the antiperspirant component reduces sweating.

Depending on the other components and their amounts, it may be desirable for the composition to further include an anti-irritation component. The anti-irritation component may be selected from but not be limited to allantoin, bisabolol, glycol-modified hydroxyphenyl propamidobenzoic acid compounds, betaine, chamomile, ginger, oat, hydrocortisone, calamine, aloe vera, witch hazel, acacia, almond, angelica, arnica, avocado, basil, chrysanthemum, clove, cocoa, cucumber, echinacea, fennel, ginseng, henna, honey, honeysuckle flower, jasmine, juniper, lemongrass, mallow, nutgrass (motha) root, olive, peppermint, pueraria root, rooibos, rosemary, shea butter, seaweed, sophora flower wheat and other botanical extracts and mixtures of one or more such components. The compositions of the invention may further include a silicone component. The silicone component is selected to be in a form compatible with the single phase of the temperature management composition. The silicone component may be selected from one or more of the following groups of silicones: dimethicones, cyclomethicones, silicone polyethers, silicone quaternary compounds, silicone amines, silicone phosphates, silicone betaines, silicone amine oxides, alkylated silicones, alkylated silicone polyethers, fluorinated silicones, silicone polyether esters, silicone carboxylates and polydimethylsiloxanes.

The present invention is also related to a method for providing a skin cooling effect to upper torso of a human. The method includes a step of applying an amount of a temperature management composition to a skin area of a user. The temperature management composition includes from 0.01 to 10% by weight of a neurosensory agent and from 0.01% to 30% by weight of an antiperspirant component. The composition also includes a polar carrier comprising water and a monohydric alcohol. The ratio of water to monohydric alcohol is from 0.0625:1 to 1.5:1. Further, the composition has a viscosity at room temperature of less than 2500 centipoise. The method of the invention also includes a step of repeating the application step after a period of time as needed to provide additional skin cooling effect. Typically, the temperature management composition will be applied prophylactically by the user—meaning the user will apply the composition prior to going to bed in order to prevent and/or mitigate the symptoms of a hot flash that the user may experience during the nighttime. If the user wakes during the night, the user may apply the composition again if they feel the initial effect and/or benefit has worn off.

These aspects and additional aspects of the invention will be described in greater detail herein. Further, it is to be understood that both the foregoing general description and the following detailed description are exemplary and are intended to provide further explanation of the invention claimed.

BRIEF DESCRIPTION OF THE DRAWING

A full and enabling disclosure of the present invention, including the best mode thereof, directed to one of ordinary skill in the art, is set forth more particularly in the remainder of the specification, which makes reference to the appended figure in which:

FIG. 1 is a plot of Percent (Weight) Evaporation versus Time.

DETAILED DESCRIPTION OF THE INVENTION

The present disclosure of the invention will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The compositions of the present invention are single phase compositions that are intended to be provided in packaging that enables them to be sprayed onto the user's skin. The compositions of the invention may also be wiped onto the skin by transfer from a substrate onto which the compositions have been applied. The compositions of the invention do not require a propellant for delivery. Therefore, it may be desirable to provide the compositions of the invention in non-aerosol packaging. Use of the compositions of the present invention provides a method of alleviating discomfort experienced by a woman during a hot flash that occurs during menopause including alleviating the feeling of intense heat. Use of the compositions of the present invention further provides a method of alleviating symptoms of physical discomfort resulting from increased heart rate and digital blood flow associated with hot flashes. The methods of the present invention include the step of applying a temperature management composition. The compositions of the invention may be applied over a large area of skin surface of the user. For example, the compositions may be applied to the face, neck, shoulders, arms and chest. The compositions may also be applied to any other areas of the body that may benefit from the comfort provided. Typically, the compositions are applied prophylactically—that is, they are applied by the user before the user goes to bed for the night. The compositions are applied to prevent and/or mitigate any of the symptoms/effects of a hot flash. If necessary to provide a sustained cooling effect, the compositions may be re-applied by the user if the user wakes during the night.

The compositions of the invention may be applied to the targeted skin surfaces either directly, in liquid form, such as by a spray bottle, roll-on applicator or similar packaging capable of delivering a liquid composition in a relatively uniform amount over the full surface to be covered. Alternatively, the compositions of the invention may be applied to the targeted skin surfaces by a carrier, such as a basesheet (i.e. a "wet" wipe or towelette). Because the compositions are liquid at room temperature, the composition may be applied to skin surfaces by wiping the surfaces with a basesheet that has been saturated with the composition; the composition will transfer from the basesheet to the skin surface. The basesheet may be formed from one or more woven materials, nonwoven materials, cellulosic materials and combinations of such materials. More specifically, the basesheet may be formed of nonwoven fibrous sheet materials that include meltblown, spunlace, coform, air-laid, bonded-carded web materials, hydroentangled materials and combinations of such materials. Such materials can be made of synthetic or natural fibers or a combination of such fibers. Typically, the basesheet will have a basis weight of from 25 grams per square meter to 120 grams per square meter and desirably from 40 grams per square meter to 90 grams per square meter.

The basesheet may be constructed of a coform material of polymer fibers and absorbent fibers having a basis weight of from 45 to 80 grams per square meter and desirably 60 grams per square meter. Typically, such coform basesheets are constructed of a gas-formed matrix of thermoplastic polymeric meltblown fibers and cellulosic fibers. Various suitable materials may be used to provide the polymeric meltblown fibers, such as, for example, polypropylene microfibers. Alternatively, the polymeric meltblown fibers may be elastomeric polymer fibers, such as those provided by a polymer resin. For instance, VISTAMAXX elastic olefin copolymer resin designated PLTD-1810, available from ExxonMobil Corporation of Houston, Tex., or KRATON G-2755, available from Kraton Polymers of Houston, Tex., may be used to provide stretchable polymeric meltblown fibers for the coform basesheets. Other suitable polymeric materials or combinations thereof may alternatively be utilized as known in the art.

The coform basesheet additionally may be constructed of various absorbent cellulosic fibers, such as, for example, wood pulp fibers. Suitable commercially available cellulosic fibers for use in the coform basesheets can include, for example, NF 405, which is a chemically treated bleached southern softwood Kraft pulp, available from Weyerhaeuser Co. of Washington, D.C.; NB 416, which is a bleached southern softwood Kraft pulp, available from Weyerhaeuser Co.; CR-0056, which is a fully debonded softwood pulp, available from Bowater, Inc. of Greenville, S.C.; Golden Isles 4822 debonded softwood pulp, available from Koch Cellulose of Brunswick, Ga.; and SULPHATATE HJ, which is a chemically modified hardwood pulp, available from Rayonier, Inc. of Jessup, Ga. The relative percentages of the polymeric meltblown fibers and cellulosic fibers in the coform basesheet may vary over a wide range depending upon the desired characteristics of the wipes. For example, the coform basesheet may have from 10 weight percent to 90 weight percent, desirably from 20 weight percent to 60 weight percent, and more desirably from 25 weight percent to 35 weight percent of polymeric meltblown fibers based on the dry weight of the coform basesheet.

The compositions of the invention may be incorporated into the basesheet in an add-on amount of from 50% (by weight of the basesheet) to 800% (by weight of the basesheet). More specifically, the compositions may be incorporated into the basesheet in an add-on amount of from 200% (by weight of the basesheet) to 600% (by weight of the basesheet) or from 400% (by weight of the basesheet) to 600% (by weight of the basesheet). The composition add-on amounts may vary depending on the composition of the basesheet.

The temperature management compositions of the invention include a neurosensory agent. Among other benefits, the neurosensory component provides a cooling effect. The neurosensory component may be selected from menthol, menthyl lactate, menthyl PCA, menthyl succinate, menthyl acetate, menthyl safflowerseedate, menthyl salicylate, N,2,3-trimethyl-2-isopropyl butanamide, N-ethyl-p-menthan-3-carboxamide, 3-(1-menthoxy)propane-1,2-diol, 1-(2-hydroxyphenyl)-4-(3-nitrophenyl)-1,2,3,6-tetrahydropyridine-2-one, 2-(2-alkoxy-I-methylethyl)-5-methyl cyclohexanols, 1-menthanyl carbonates and mixtures of one or more of these compounds. Desirably, the compositions of the invention include from 0.01% to 10% by weight of one or more neurosensory agents.

The temperature management compositions of the invention also include an antiperspirant component. Among other benefits, the antiperspirant component reduces sweating by the user. The antiperspirant component may be selected from aluminum chlorohydrate, aluminum dichlorohydrate, aluminum susquichlorohydrate, aluminum chlorohydrex PG, aluminum dichlorohydrex PG, aluminum susquichlorohydrex PG, aluminum chlorohydrex PEG, aluminum dichlorohydrex PEG, aluminum susquichlorohydrex PEG, aluminum chloride, aluminum-zirconium trichlorohydrate, aluminum-zirconium tetrachlorohydrate, aluminum-zirconium pentachlorohydrate, aluminum-zirconium octachlorohydrate, aluminum-zirconium trichlorohydrex GLY, aluminum-zirconium tetrachlorohydrex GLY, aluminum-zirconium pentachlorohydrex GLY, aluminum-zirconium octachlorohydrex GLY and mixtures of one or more of these compounds. Desirably, the compositions of the invention include from 0.01% to 30% by weight of one or more antiperspirant components.

The temperature management compositions of the invention further include a polar carrier including water and a monohydric alcohol. The compositions of the invention feature a particular range of ratios of water to monohydric alcohol. In particular, the compositions of the invention have a ratio range of the proportion of water to monohydric alcohol of from 0.0625:1 to 1.5:1. The left side of the ratio represents the relative amount of water to a single "unit" of monohydric alcohol on the right side of the ratio. The inventors unexpectedly found that a proportion of water to monohydric alcohol in this range provides solubility of the neurosensory agent in the presence of the specified amount of antiperspirant component resulting in a final composition that is one phase and does not irritate the skin of the user. A monohydric alcohol contains only one hydroxyl group in each molecule. Three of the four simplest alcohols form a series in which the number of carbon and hydrogen atoms in the molecule increases progressively, each one having an extra $CH_2$ (methylene) group: ethanol (ethyl alcohol, $C_2H_5OH$); propanol (propyl alcohol, $C_3H_7OH$); and butanol (butyl alcohol, $C_4H_9OH$); each one of these monohydric alcohols is suitable for purposes of the compositions of the present invention. Straight and branched forms of these monohydric alcohols are suitable. In order to achieve the desired proportion of water to monohydric alcohol, the compositions of the invention may contain from 6% to 70% by weight of water and from 30% to 94% by weight of monohydric alcohol.

In order to be easily applied to the skin at room temperature and to be capable of application without the use of a propellant, the temperature management compositions of the invention have a viscosity at room temperature of less than 2500 centipoise. Having a viscosity of less than 2500 centipoise also enables application of the compositions to the end user's skin from a wet wipe substrate.

While the temperature management compositions of the invention are non-irritating, compositions containing greater than 50% by weight monohydric alcohol have the potential to cause minor skin irritation. To the extent such minor irritation may occur, the compositions of the invention may also include an anti-irritation component. Suitable anti-irritation components may be selected from but not be limited to allantoin, bisabolol, glycol-modified hydroxyphenyl propamidobenzoic acid compounds, betaine, chamomile, ginger, oat, hydrocortisone, calamine, aloe vera, witch hazel, acacia, almond, angelica, arnica, avocado, basil, chrysanthemum, clove, cocoa, cucumber, echinacea, fennel, ginseng, henna, honey, honeysuckle flower, jasmine, juniper, lemongrass, mallow, nutgrass (motha) root, olive, peppermint, pueraria root, rooibos, rosemary, shea butter, seaweed, sophora flower wheat, other botanical extracts and mixtures of one or more such anti-irritation components. If incorporated, the compositions of the invention may include from 0.01% to 5% by weight of an anti-irritation component.

Further, the temperature management compositions of the invention may further include a silicone component in a form compatible with a single phase composition. The silicone component may be selected from one or more of the following groups of silicones: dimethicones, cyclomethicones, silicone polyethers, silicone quaternary compounds, silicone amines, silicone phosphates, silicone betaines, silicone amine oxides, alkylated silicones, alkylated silicone polyethers, fluorinated silicones, silicone polyether esters, silicone carboxylates and polydimethylsiloxanes.

In addition to the components described herein, the compositions of the invention may also include one or more fragrances, botanicals, pH adjusters, preservatives, dyes, builders, compatible surfactants, cleansing components and other components known to be useful in cosmetic compositions. Any additional components should be selected to be compatible with the aqueous, single phase nature of the other components. Desirably, any additional components should not necessarily cause the overall composition to require a propellant for application to the skin. The compositions of the invention may include from 0.01% by weight to 10% by weight of one or more of these supplemental components.

In order to test the benefits provided by compositions of the invention, a study with prospective users of the compositions was conducted. Two compositions representative of the invention were evaluated. The specific components of each composition are provided in Table 1 below.

TABLE 1

| Component | INCI/Trade Name | Composition #1 Code "K-125-19" % by weight | Composition #2 Code "K-215-20" % by weight |
|---|---|---|---|
| Water | | 11.86 | 30.96 |
| Aluminum Chlorohydrate | REACH 501 Aluminum chlorohydrate available from Reheis, Inc. | 10.00 | 10.00 |
| Allantoin | Allantoin | 0.10 | 0.10 |
| Hydroxyethyl Urea | HYDROVANCE Hydroxyethyl urea available from AkzoNobel | 2.00 | 2.00 |
| Menthyl lactate | FRESCOLAT ML crystals available from Symrise AG | 1.00 | 1.00 |
| PEG-75 Lanolin | SOLAN E PEG-75 lanolin available from B&K Technology | — | 0.15 |
| Polysorbate 20 | TWEEN 20 solution available from Croda | — | 0.10 |
| Bis-PEG-18 Methyl Ether Dimethyl Silane | 2501 cosmetic wax available from Dow Corning | 10.00 | — |
| PEG-7 glyceryl cocoate | GLYCEROX HE nonionic hydrophilic ester available from Croda | 2.00 | 0.15 |
| Butylene glycol, Pentylene glycol, Hydroxyphenyl propamidobenzoic acid | SYMCALMIN 143535 anti-irritant Available from Symrise AG | 0.50 | — |
| Ethanol | SDA 40B, 190 Proof Ethanol available from Equistar | 62.00 | 55.00 |
| Glycerin and *Aloe Barbadensis* leaf extract | ACTIPHYTE *Aloe Vera* 10 Fold GL 100 NP available from Active Organics, Inc. | 0.01 | 0.01 |
| Glycerin and *Prunus Amygdalus Dulcis* (Sweet Almond) extract | ACTIPHYTE Almond GL 100 NP available from Active Organics, Inc. | 0.01 | 0.01 |
| Fragrance | Fragrance available from Firmenich | 0.50 | 0.50 |
| Tocopheryl Acetate | VITAMIN E ACETATE available from DSM Nutritional Products | 0.02 | 0.02 |

Each of these compositions was evaluated by prospective users. The results of the evaluation are provided in Table 2 below.

TABLE 2

| | Frequency K-125-19 | K-125-19 % | Frequency K-215-20 | K-215-20 % |
|---|---|---|---|---|
| Night sweats discomfort disappeared | 16 | 28% | 15 | 26% |
| Night sweats discomfort was reduced a lot | 31 | 53% | 31 | 53% |
| Night sweats discomfort was reduced significantly | 9 | 16% | 11 | 19% |
| Night sweats discomfort was reduced a little | 1 | 2% | 0 | 0% |
| Night sweats discomfort wasn't reduced | 1 | 2% | 1 | 2% |
| Total | 58 | 100% | 58 | 100% |

While Composition #2 provided the desired cooling and antiperspirant effects, this composition had the potential to cause minor skin irritation because it contained at least 50% monohydric alcohol. In order to eliminate any possible skin irritation, the composition was modified to include an anti-irritation component, SYMCALMIN 143535 anti-irritant available from Symrise AG (as also used in Composition #1). A representative example of the modified composition of the invention is provided in Table 3 below. The modified composition may be prepared by adding the water and PEG-75 Lanolin to a mixing vessel. These components may be blended by mixing at a speed of 150 rpm and heating to a temperature of 50° C., or until the PEG-75 Lanolin melts. After the PEG-75 Lanolin melts and the components are blended, the composition may be cooled. Next, the aluminum chlorohydrate, allantoin, hydroxyethyl urea and PEG-7 glyceryl cocoate may be added to the mixing vessel and mixing continued. After these components are incorporated, the ethanol may be added to the mixing vessel. After the ethanol is incorporated, the Betaine may be added followed by the SYMCALMIN anti-irritant. The polysorbate 20, fragrance and Vitamin E may be pre-mixed together and then added to the mixing vessel while mixing continues. Finally, the aloe extract and sweet almond extract may be added to the mixing vessel to produce the finished composition.

TABLE 3

| Component | INCI/Trade Name | Composition #3 Code "K-215-28" % by weight |
|---|---|---|
| Water | | 29.96 |
| Aluminum Chlorohydrate | REACH 501 Aluminum chlorohydrate available from Reheis, Inc. | 10.00 |
| Allantoin | Allantoin | 0.10 |
| Hydroxyethyl Urea | HYDROVANCE Hydroxyethyl urea available from AkzoNobel | 2.00 |
| Menthyl lactate | FRESCOLAT ML crystals available from Symrise AG | 1.00 |
| PEG-75 Lanolin | SOLAN E PEG-75 lanolin available from B&K Technology | 0.15 |
| Polysorbate 20 | TWEEN 20 solution available from Croda | 0.10 |
| PEG-7 glyceryl cocoate | GLYCEROX HE nonionic hydrophilic ester available from Croda | 0.15 |
| Ethanol | SDA 40B, 190 Proof Ethanol available from Equistar | 55.00 |
| Butylene glycol, Pentylene glycol, Hydroxyphenyl propamidobenzoic acid | SYMCALMIN 143535 anti-irritant Available from Symrise AG | 1.00 |
| Glycerin and *Aloe Barbadensis* leaf extract | ACTIPHYTE *Aloe Vera* 10 Fold GL 100 NP available from Active Organics, Inc. | 0.01 |
| Glycerin and *Prunus Amygdalus Dulcis* (Sweet Almond) extract | ACTIPHYTE Almond GL 100 NP available from Active Organics, Inc. | 0.01 |
| Fragrance | Fragrance available from Givaudan | 0.50 |
| Tocopheryl Acetate | VITAMIN E ACETATE available from DSM Nutritional Products | 0.02 |

The consumer impression and experience with the temperature management composition defined in Table 3 was very positive. Consumers found the composition of Table 3 to provide several benefits after use for fourteen days. The percentages in Table 4 below represent the percentage of respondents who noticed improvement in their skin after fourteen days of product use and who agreed with the relevant product statements. There were fifty-six participants in the study and participants were instructed to apply the composition to the parts of their skin experiencing night sweats.

TABLE 4

| Statements | T14 (%) |
|---|---|
| "The product does not make the skin dry" | 89.3 |
| "Product use helps reduce sweating" | 100.0 |
| "Product use helps reduce sweating that interrupts my sleep" | 83.9 |
| "The product provides a fresh sensation for the skin" | 96.4 |
| "Product use helps to keep me fresh at night" | 96.4 |
| "Product use makes me sleep calmer" | 94.6 |
| "Product use makes me have a calmer rest" | 96.4 |
| "Product use helps to keep me fresh at night, providing me a calm rest" | 98.2 |

The table presents the percentage of subjects who totally agreed or agreed with the statements above.

One of the benefits of the compositions of the present invention is the solubility of the neurosensory agent (to form a homogenous, single phase composition) in a composition with up to 30% of the antiperspirant component. The solubility of the neurosensory agent is achieved by providing a polar carrier with a ratio of water to monohydric alcohol within a range of from 0.0625:1 to 1.5:1. The range of ratios of water to monohydric alcohol were established by experimenting with the solubility of representative neurosensory agents in different mixtures of water and monohydric alcohol. The results are provided in the Table 5 below.

TABLE 5

| | Main Formulation | | Solubility of Menthyl Derivatives in independent Main Formulation batches | | | | |
|---|---|---|---|---|---|---|---|
| Ratio Water:Alcohol | | | 1% Menthyl Lactate | 1% Menthyl PCA Liquid | 1% Menthyl Succinate | 1% Menthyl Acetate | 1% Menthyl PCA + Menthol |
| 0:1 | 4% Additional Ingredients | 5% Aluminum Chlorohydrate | + | + | + | + | + |
| 0.0625:1 | | | + | + | + | + | + |
| 0.56:1 | | | + | + | + | + | + |
| 0.65:1 | | | + | + | + | + | + |
| 1:1 | | | + | + | + | +/− | + |
| 1.5:1 | | | + | − | − | − | + |
| 2:1 | | | − | − | − | − | − |
| 3:1 | | | − | − | − | − | − |
| 4:1 | | | − | − | − | − | − |
| 1:0 | | | − | − | − | − | − |
| 0.5:1 | 4% Additional Ingredients | 5% Aluminum Chlorohydrate | + | + | + | + | + |
| 1:1 | | | + | + | + | + | + |
| 1.5:1 | | | + | + | +/− | +/− | + |
| 2:1 | | | +/− | + | − | − | + |
| 3:1 | | | − | − | − | − | − |
| 4:1 | | | − | − | − | − | − |
| 5:1 | | | − | − | − | − | − |
| 37.5:0 | | | − | − | − | − | − |
| 0:1 | 4% Additional Ingredients | 0.5% Aluminum Chlorohydrate | + | + | + | + | + |
| 0.0625:1 | | | + | + | + | + | + |
| 0.5:1 | | | + | + | + | + | + |
| 1:1 | | | + | + | + | + | + |
| 1.5:1 | | | + | + | − | − | + |
| 2:1 | | | − | + | − | − | + |
| 3:1 | | | − | − | − | − | − |
| 4:1 | | | − | − | − | − | − |
| 1:0 | | | − | − | − | − | − |

In Table 5 above, the first "main formulation" includes 5% by weight aluminum chlorohydrate as the antiperspirant component. Five different neurosensory agents (each a menthol derivative) were evaluated for their solubility in the "main formulation"; in each instance, the neurosensory agent was present in an amount of 1% by weight. After accounting for the 4% of additional ingredients, the remainder of each formulation is a relative amount of water and monohydric alcohol consistent with the indicated ratio. The "+" sign indicates that the neurosensory agent was completely soluble and formed a homogenous phase with the "main formulation". The "−" sign indicates that the neurosensory was not fully soluble within the "main formulation"; a "+/−" indicates that the combination of the neurosensory agent and the "main formulation" had a cloudy appearance—but was still a homogenous phase. With the first "main formulation" (having 5% by weight aluminum chlorohydrate), the neurosensory agent was soluble up to a ratio of 1.5:1 of water to monohydric alcohol. For purpose of explanation, in the first row of the first "main formulation", the composition has a water to monohydric alcohol ratio of 0:1; this indicates a composition with 0% by weight water and 90% by weight monohydric alcohol. With the second "main formulation" (having 25% by weight aluminum chlorohydrate), the neurosensory agent was soluble up to a ratio of 2:1 of water to monohydric alcohol. With the third "main formulation" (having 0.5% by weight aluminum chlorohydrate), the neurosensory agent was soluble up to a ratio of 2:1 of water to monohydric alcohol.

When the compositions of the invention are used by a consumer, the composition is desirably applied to the body with no feeling of wetness while providing the benefits of cooling and antiperspirant, with no irritation. Understanding how the product dries on the consumer's skin is very important in understanding how the product will be perceived. To understand this concept, the dry time of different application methods was evaluated using a moisture analyzer. A moisture analyzer takes a known weight of a liquid sample and applies a specified heat to the sample. As the sample evaporates, the weight/% loss is recorded. Exemplary Composition #3 (described in Table 3 above) was measured at 40° C. as this was the closest temperature the instrument would allow that was nearest body temperature (37° C.). Because a suitable dry time is best achieved with spray delivery, Composition #3 was evaluated for three different spray application methods: drop application, pump spray application and dry sprayer application. The moisture analyzer required an aluminum weigh boat be placed over heating coils. The moisture analyzer contained an internal balance so that sample weights could be determined before and during heating. The aluminum weigh boat was placed over the heating element and sample was added. The samples were analyzed (heated) for 5 minutes. Samples were added via the three application methods at 1 gram amounts: drop-wise, pump spray and dry sprayer. The exact starting weights were drop=1.105 g, pump=1.175 g and dry spray=1.116 g. Although the starting weights differed, the evaporation rate was recorded as a percentage of the initial weight. As can be seen in FIG. 1, drop application of the formulation produced the slowest dry time followed by the pump spray application and lastly, the dry sprayer application. The pump spray and drop applications were still drying at the end of the 5 minute evaluation. The dry sprayer application sample completely dried before the 5 minute period; no change in sample weight was noticed after 3.1 minutes. This difference in dry time is believed to be due to the optimization of the particle size of the applied composition. The dry sprayer application produces a very small particle size to the surface thus allowing the formulation to dry faster than the other methods of application. The pump sprayer had a larger particle size applied and the drop application actually produced a thin film during application. Particle size of the pump sprayer averaged 240 μm (microns) in a range from 5 μm (microns) to 900 μm (microns). The dry sprayer application produced a particle size of 34 μm (microns) to 41 μm (microns). Desirably, when the compositions of the invention are applied, the particle size may range from 1 μm (microns) to 1000 μm (microns). More specifically, the preferred particle size upon application of the compositions is from 10 μm (microns) to 500 μm (microns) and even more specifically, from 20 μm (microns) to 200 μm (microns). With the desired ranges, the average particle size would need to average more than 10-20 μm (microns) as to avoid any inhalation concerns.

While the compositions of the invention have been described in detail with respect to specific aspects thereof, it will be appreciated that those skilled in the art, upon attaining an understanding of the foregoing, may readily conceive of alterations to, variations of and equivalents to these compositions. Accordingly, the scope of the present invention should be assessed as that of the claims and any equivalents thereto.

We claim:

1. A single phase temperature management composition comprising:

(a) from 0.01% to 10% by weight of a neurosensory agent;

(b) from 0.01% to 30% by weight of an antiperspirant component; and (c) a polar carrier comprising water and a monohydric alcohol in a ratio of water to monohydric alcohol of from 0.0625:1 to 0.65:1 wherein the composition has a viscosity at room temperature of less than 2500 centipoise;

wherein the composition does not comprise a propellant.

2. The temperature management composition of claim 1 wherein the neurosensory agent is selected from menthol, menthyl lactate, menthyl PCA, menthyl succinate, menthyl acetate, menthyl safflowerseedate, menthyl salicylate, N,2,3-trimethyl-2-isopropyl butanamide, N-ethyl-p-menthan-3-carboxamide, 3-1-menthoxy propane-1,2-diol, 1-(2-hydroxyphenyl)-4-(3-nitrophenyl)-1,2,3,6-tetrahydropyriidine-2-one, 2-(2-alkoxy-lmethylethyl)-5-methyl cyclohexanols, 1-menthanyl carbonates and mixtures thereof.

3. The temperature management composition of claim 1 wherein the antiperspirant component is selected from aluminum chlorohydrate, aluminum dichlorohydrate, aluminum susquichlorohydrate, aluminum chlorohydrex PG, aluminum dichlorohydrex PG, aluminum susquichlorohydrex PG, aluminum chlorohydrex PEG, aluminum dichlorohydrex PEG, aluminum susquichlorohydrex PEG, aluminum chloride, aluminum-zirconium trichlorohydrate, aluminum-zirconium tetrachlorohydrate, aluminum-zirconium pentachlorohydrate, aluminum zirconium octachlorohydrate, aluminum-zirconium trichlorohydrex GLY, aluminum-zirconium tetrachlorohydrex GLY, aluminum-zirconium pentachlorohydrex GLY, aluminum-zirconium octachlorohydrex GLY and mixtures thereof.

4. The temperature management composition of claim 1 wherein the monohydric alcohol is selected from ethanol, propanol, isopropanol and butanol.

5. The temperature management composition of claim 1 wherein the composition further comprises an anti-irritation component selected from allantoin, bisabolol, glycol-modified hydroxyphenyl propamidobenzoic acid compounds, betaine, chamomile, ginger, oat, hydrocortisone, calamine, aloe vera, witch hazel, acacia, almond, angelica, arnica, avocado, basil, chrysanthemum, clove, cocoa, cucumber, echinacea, fennel, ginseng, henna, honey, honeysuckle flower, jasmine, juniper, lemongrass, mallow, nutgrass (motha) root, olive, peppermint, pueraria root, rooibos, rosemary, shea butter, seaweed, sophora flower wheat and mixtures of such anti-irritation components.

6. The temperature management composition of claim 5 wherein the composition includes from 0.01 to 5% by weight of the anti-irritation component.

7. The temperature management composition of claim 1 further comprising a silicone component compatible with the single phase temperature management composition.

8. The temperature management composition of claim 7 wherein the silicone component is selected from dimethicones, cyclomethicones, silicone polyethers, silicone quaternary compounds, silicone amines, silicone phosphates, silicone betaines, silicone amine oxides, alkylated silicones, alkylated silicone polyethers, fluorinated silicones, silicone polyether esters, silicone carboxylates, polydimethylsiloxanes and mixtures of such silicone components.

9. The temperature management composition of claim 1 wherein the antiperspirant component is based on aluminum or aluminum-zirconium.

10. A non-aerosol, single phase temperature management composition comprising:

(a) from 0.01% to 10% by weight of a neurosensory agent;

(b) from 0.01% to 30% by weight of an antiperspirant component;

(c) a polar carrier comprising water and a monohydric alcohol in a ratio of water to monohydric alcohol of from 0.0625:1 to 0.65:1 wherein the composition has a viscosity at room temperature of less than 2500 centipoise.

* * * * *